(12) United States Patent
Lumma et al.

(10) Patent No.: US 7,654,739 B2
(45) Date of Patent: Feb. 2, 2010

(54) X-RAY EQUIPMENT AND METHOD FOR CONTROLLING IT

(75) Inventors: Waldemar Lumma, Hamburg (DE); Horst-Hartwig Schwieker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 195 days.

(21) Appl. No.: 11/571,578

(22) PCT Filed: Jul. 4, 2005

(86) PCT No.: PCT/IB2005/052214

§ 371 (c)(1),
(2), (4) Date: Jan. 3, 2007

(87) PCT Pub. No.: WO2006/008677

PCT Pub. Date: Jan. 26, 2006

(65) Prior Publication Data

US 2008/0285723 A1 Nov. 20, 2008

(30) Foreign Application Priority Data

Jul. 13, 2004 (EP) .................................. 04103310

(51) Int. Cl.
*A61B 6/08* (2006.01)
(52) U.S. Cl. .................. 378/205; 378/197; 378/116
(58) Field of Classification Search ......... 378/114–117, 378/193, 195–197, 205, 208, 209
See application file for complete search history.

(56) References Cited

U.S. PATENT DOCUMENTS

| | | | |
|---|---|---|---|
| 6,402,373 B1 | 6/2002 | Polkus et al. | |
| 6,412,978 B1 | 7/2002 | Watanabe et al. | |
| 6,702,459 B2 * | 3/2004 | Barnes et al. | ............... 378/197 |
| 2002/0122534 A1 | 9/2002 | Polkus et al. | |
| 2002/0150215 A1 | 10/2002 | Barnes et al. | |
| 2003/0091156 A1 | 5/2003 | Crain et al. | |
| 2003/0194056 A1 | 10/2003 | Spahn | |

FOREIGN PATENT DOCUMENTS

| | | |
|---|---|---|
| DE | 9012435 | 2/1992 |
| EP | 1004271 A1 | 5/2000 |
| EP | 1245188 A2 | 10/2002 |
| WO | 2004052207 A1 | 6/2004 |

* cited by examiner

*Primary Examiner*—Jurie Yun

(57) ABSTRACT

X-ray equipment in which the X-ray source and X-ray detector can be moved in a simple and uncomplicated manner permits an X-ray picture to be taken only when the X-ray source and X-ray detector are aligned to match one another. This provides the user with information about how this appropriate alignment can be achieved, which helps to avoid failed exposures, and which conforms to radiation hygiene. The X-ray equipment comprises:
  an evaluation device for determining a suitable trigger setting for an X-ray picture, in which the X-ray source and detector have such positions and alignments that an X-ray picture of the examination object can be taken using the X-ray equipment;
  a signal device for outputting signals that inform a user how a trigger setting is to be achieved; and
  a release device for releasing the X-ray equipment for an X-ray picture when the X-ray equipment has a trigger setting.

20 Claims, 3 Drawing Sheets

X-RAY EQUIPMENT AND METHOD FOR CONTROLLING IT

The invention relates to X-ray equipment with an X-ray source that can be altered in respect of its position and/or alignment, an aperture arrangement, a positioning device for positioning an object that is to be examined, an X-ray detector that can be altered in respect of its position and/or alignment, and a detection device for detecting the position and/or alignment of the X-ray source and/or of the X-ray detector. The invention also relates to a method for controlling the X-ray equipment.

From the German utility model DE-90 12 435 U1, we know of such X-ray equipment. The X-ray source and X-ray detector can be moved by means of adjusting slides, wherein position transmitters and adjusting elements are provided for determining or altering the spatial alignment of the X-ray source and X-ray detector. In DE-90 12 435 U1, it is proposed that the adjusting elements are acted on in such a way that a central axis of the X-ray source and a central axis of the X-ray detector coincide with one another. In the case of this X-ray equipment, it turns out to be disadvantageous that due to the combination of position transmitters and adjusting elements, it is very elaborate, and that furthermore the spatial alignment of the X-ray source and X-ray detector via a control desk and a computer is difficult and time-consuming.

European patent application EP 1 004 271 A1 likewise presents X-ray equipment as described above. The X-ray source and X-ray detector are movable, wherein via a control unit it is ensured that they are always aligned relative to one another in such a way that an X-ray picture is possible. In one embodiment, the X-ray source or the X-ray detector can be moved manually, and the control unit automatically guides the corresponding counterpart to follow it, in such a way that the source and the detector remain appropriately aligned to one another. With this system too, one disadvantage is the great expense that is required for determining the alignment and for the automatic movement.

US disclosure document US 2003/0194056 A1 discloses another X-ray system of the type named at the outset. Here, the X-ray source and the X-ray detector can be moved freely; release for taking an X-ray picture is given only when the X-ray source and the X-ray detector are aligned appropriately to one another for a desired X-ray picture. It proves to be a disadvantage here that the user is given no assistance by means of which he can find the appropriate alignment of X-ray source and X-ray detector that allows him to take an X-ray picture.

It is thus an object of the invention to define X-ray equipment of the type named in the introduction, in which the X-ray source and the X-ray detector can be moved in a simple and uncomplicated way, which permits an X-ray picture to be taken only when the X-ray source and X-ray detector are aligned to match one another, and which gives the user information about how this appropriate alignment can be achieved. The intention is to avoid failed exposures, and radiation hygiene is to be observed.

To achieve the object stated above, in the case of the X-ray equipment named at the outset, an evaluation device is provided for determining a trigger setting that is suitable for an X-ray picture, in which the X-ray source and the X-ray detector have such positions and alignments that an X-ray picture of the examination object can be taken using the X-ray equipment; also provided are a signal device for outputting signals that inform a user how a trigger setting is to be achieved, and a release device for releasing the X-ray equipment for an X-ray picture when the X-ray equipment has a trigger setting.

The invention is based on the idea that by determining the spatial data of the X-ray source and the X-ray detector, their position and alignment are not only compared with a desired or permitted position and alignment to see whether an X-ray picture of an examination object is possible, but that through the use of the current positions and alignments, it is possible both to determine trigger settings and to provide instructions about what changes to the settings for the X-ray equipment, for example to the position or alignment, are necessary in order to achieve a trigger setting. To safely achieve an X-ray picture, the X-ray source and X-ray detector must be aligned so that their middle verticals coincide. On the basis of a known, fixed aperture setting, a spatial distance between source and detector results, in which the detector can be used completely.

In a preferred design, the X-ray equipment according to the invention also has an adjustable aperture arrangement as well as a detection device for detecting the setting of the aperture arrangement. The evaluation device is provided in order to include, for the determination of a trigger setting, the setting of the aperture arrangement too. The trigger setting is thus one in which the X-ray source and the X-ray detector have such positions and alignments, and the aperture arrangement has such a setting, that an X-ray picture of the examination object can be taken using the X-ray equipment. Through the inclusion of a variable aperture setting in the determination of a trigger setting and a corresponding outputting of signals relating to how this trigger setting is to be achieved, including with changes to the setting of the aperture arrangement, the X-ray equipment can be used more flexibly, without entailing that through a wrong setting, only a part of the X-ray detector is exposed or used, i.e. that only a reduced resolution is achieved, or that a portion of the rays leaving the X-ray source do not hit the X-ray detector and under certain circumstances cause unnecessary radiation elsewhere.

In an advantageous design, the X-ray equipment according to the invention has an adjustable aperture arrangement, an aperture determination device for determining a trigger aperture setting that is appropriate for an X-ray picture, in which, with the X-ray source and X-ray detector in the trigger setting, an X-ray picture of the examination object can be taken using the X-ray equipment, and an aperture setting device for setting the aperture arrangement in the trigger aperture setting. With automatic setting of an aperture arrangement, the user needs only to bring the middle verticals of the X-ray source and the X-ray detector together. The setting of the aperture arrangement then takes place according to the spatial distance between the source and the detector, such that the X-ray detector it optimally utilized.

In a further development of the X-ray equipment according to the invention, also provided are a comparison device for comparing positions and/or alignments of the X-ray source and/or X-ray detector with the trigger setting, and a signal device for outputting signals that inform a user that positions and/or alignments of the X-ray source and/or X-ray detector lie in a predetermined range around the trigger setting and/or that the positions and/or alignments of the X-ray source and/or X-ray detector correspond to the trigger setting. Beyond the information about how a trigger setting is to be achieved, it is sensible for the user to obtain information about how close he is to a trigger setting, and when he has reached a trigger setting. Depending on the distance from a trigger setting, the user can then for example adjust the speed at which he moves the X-ray source or X-ray detector.

In a preferred design of the X-ray equipment according to the invention, the equipment has a brake device for fixing and/or releasing the position and/or alignment of the X-ray source and/or X-ray detector, and a control device for controlling the brake device. Once a position or alignment of the X-ray source or X-ray detector that is desired by the user has been reached, the user can fix this position or alignment by means of the control device through the brake device. A setting envisaged by the user for this is thus maintained, which makes it possible for example for him to fix the X-ray detector and then to bring the X-ray source into a trigger setting without the setting of the X-ray detector being altered in the course of this. The control device can also be subject to control by the X-ray equipment itself, i.e. it can function automatically.

The invention furthermore relates to a method for controlling X-ray equipment with an X-ray source that can be altered in respect of its position and/or alignment, an aperture arrangement, a positioning device for positioning an examination object, an X-ray detector that can be altered in respect of its position and/or alignment, with the steps:

detection of the position and/or alignment of the X-ray source and/or of the X-ray detector, determination of a trigger setting that is suitable for an X-ray picture, in which the X-ray source and the X-ray detector have such positions and alignments that an X-ray picture of the examination object can be taken using the X-ray equipment, outputting of signals that inform a user how a trigger setting is to be achieved, and release of the X-ray equipment for an X-ray picture when the X-ray equipment has a trigger setting.

These and other aspects of the invention are apparent from and will be elucidated with reference to the embodiments described hereinafter.

Figure 1:
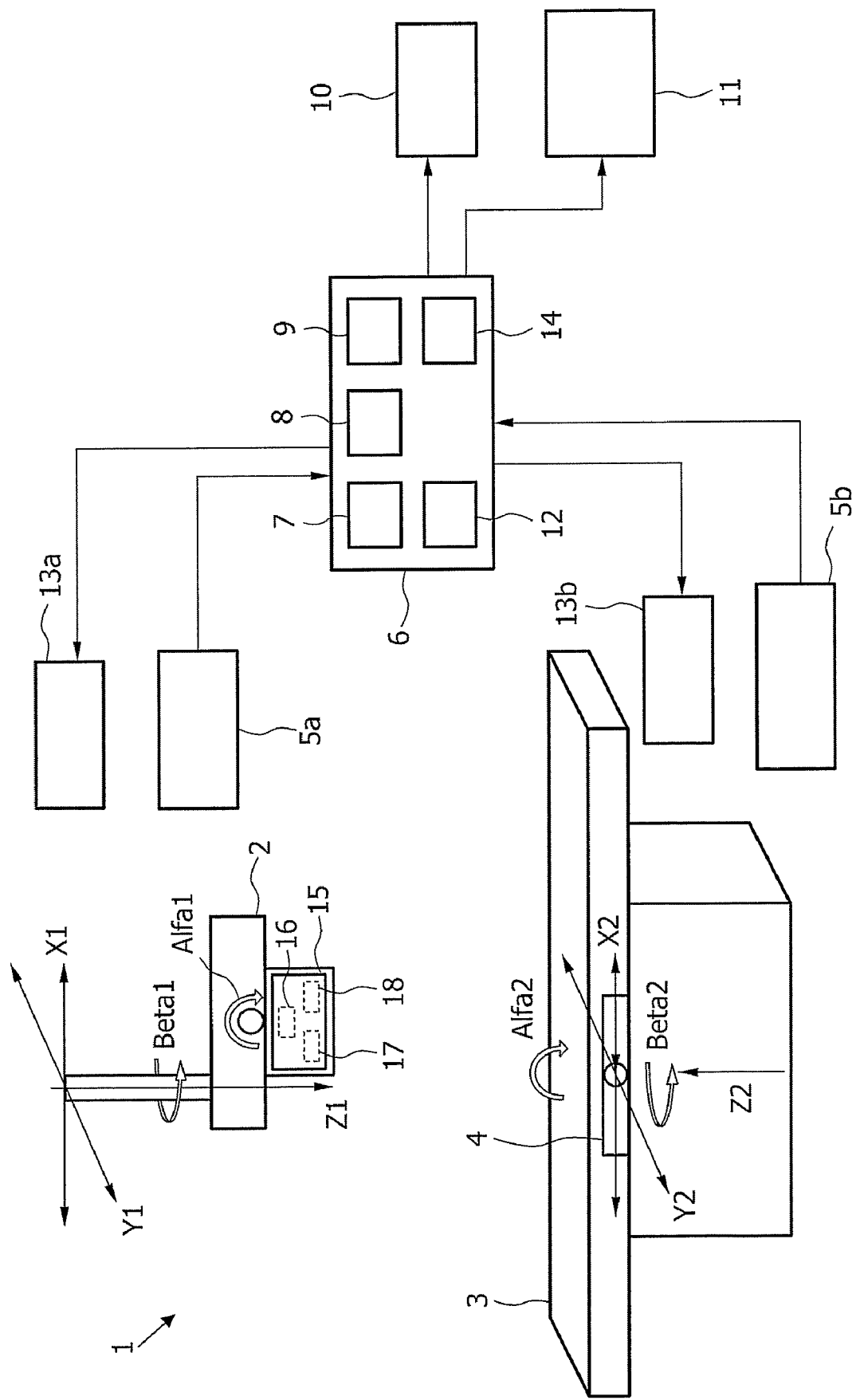
FIG. 1 shows a block diagram of X-ray equipment according to the invention.

FIG. 1 shows a block diagram of an embodiment of X-ray equipment 1 according to the invention. An X-ray source 2 can be altered in respect of position X1, Y1, Z1 and alignment Alfa1, Beta 1, and has an integrated aperture arrangement 15. Integrated into a positioning device 3 for positioning an examination object (not shown) is an X-ray detector 4 that can be altered in respect of position X2, Y2, Z2 and alignment Alfa2, Beta 2. The X-ray source 2 and X-ray detector 4 are thus movable in the three spatial directions and around 2 axes, thus making any position and alignment possible.

A detection device 5a is provided for detecting the position X1, Y1, Z1 and alignment Alfa1, Beta1 of the X-ray source 2, and a detection device 5b is provided for detecting the position X2, Y2, Z2 and alignment Alfa2, Beta2 of the X-ray detector 4.

A control unit 6 has an evaluation device 7, a comparison device 8, a signal device 9, a control device 12 and a release device 14.

The evaluation device 7 serves to determine a trigger setting that is suitable for an X-ray picture, in which the X-ray source 2 and the X-ray detector 4 have such positions X1, Y1, Z1, X2, Y2, Z2 and alignments Alfa1, Beta1, Alfa 2, Beta2 that an X-ray picture of the examination object can be taken using the X-ray equipment 1. Two trigger positions result from the fact that the X-ray source 2 or X-ray detector 4 is intended to keep its position and alignment, and the respective counterpart is to be positioned and aligned in such a way that in the event of triggering, the central beam of the X-ray bundle emitted by the X-ray source 2 coincides with the middle verticals of the detector field or of the predetermined portion of the detector field of the X-ray detector 4.

By means of the comparison device 8, the positions X1, Y1, Z1, X2, Y2, Z2 and alignments Alfa1, Beta1, Alfa2, Beta2 of the X-ray source 2 and X-ray detector 4 are compared with the trigger setting.

Via a signal device 9, signals are output by means of a display device 10 for visual display and/or by means of a loudspeaker 11 for acoustic indication, which inform a user how a trigger setting is to be achieved, and/or that the current setting is in a predetermined range around a trigger setting, or that a trigger setting has been achieved. For this, signals are envisaged that are preferably different in each case. Proximity to the trigger setting can for example be indicated by a color change from red via yellow, in the case of proximity within the predetermined range, to green in the case of correspondence, or by different sound signals. The instruction as to how a trigger position is to be reached implicitly likewise contains the instruction as to how the second trigger position is to be reached. It can however be envisaged that explicitly separate instructions are given for the changes in position and alignment of the X-ray source 2 and the X-ray detector 4, for which separate signal devices and display instruments would also be provided. Separate instructions for the individual setting possibilities can likewise be envisaged.

The control device 12 serves to control a brake device 13a for fixing the X-ray source 2 and a brake device 13b for fixing the X-ray detector 4. It can be both envisaged that the brake devices 13a and/or 13b undertake the fixing constantly and are actuated separately in order to release the fixing temporarily, or that the brake devices 13a and/or 13b fix the X-ray source 2 and the X-ray detector 4 temporarily only after separate actuation. A suitable method for fixing or locking is described in the European patent application EP 02102694.3 (PHDE 020295EP-P).

The release device 14 is provided to release the X-ray equipment 1 to take an X-ray picture when the X-ray equipment 1 has achieved a trigger setting. This release can for example consist in a power supply for the X-ray source 2 being cleared so that the X-ray source 2 can produce X-rays.

The aperture arrangement 15 can, as shown here, be integrated into the X-ray source 2, or it can also be separate from the X-ray source 2 itself. Furthermore, the aperture arrangement 15 can also be designed such that it is adjustable. A detection device 16 can then be provided for detecting the setting of the aperture arrangement, and the evaluation device 7 for determining a suitable trigger setting can be designed so as to result in a method of working analogous to that described above. Furthermore, the aperture arrangement 15 can be connected to an aperture determination device 17 for determining a suitable trigger aperture setting, and to an aperture setting device 18 for automatic setting of the aperture arrangement 15 in this trigger aperture setting, in order to enable automatic adaptation of the aperture arrangement 15 to an appropriate trigger setting of X-ray source 2 and X-ray detector 4. It can furthermore be envisaged that only one respectively predetermined portion of the overall surface of the X-ray detector 4 is used.

Figure 2:
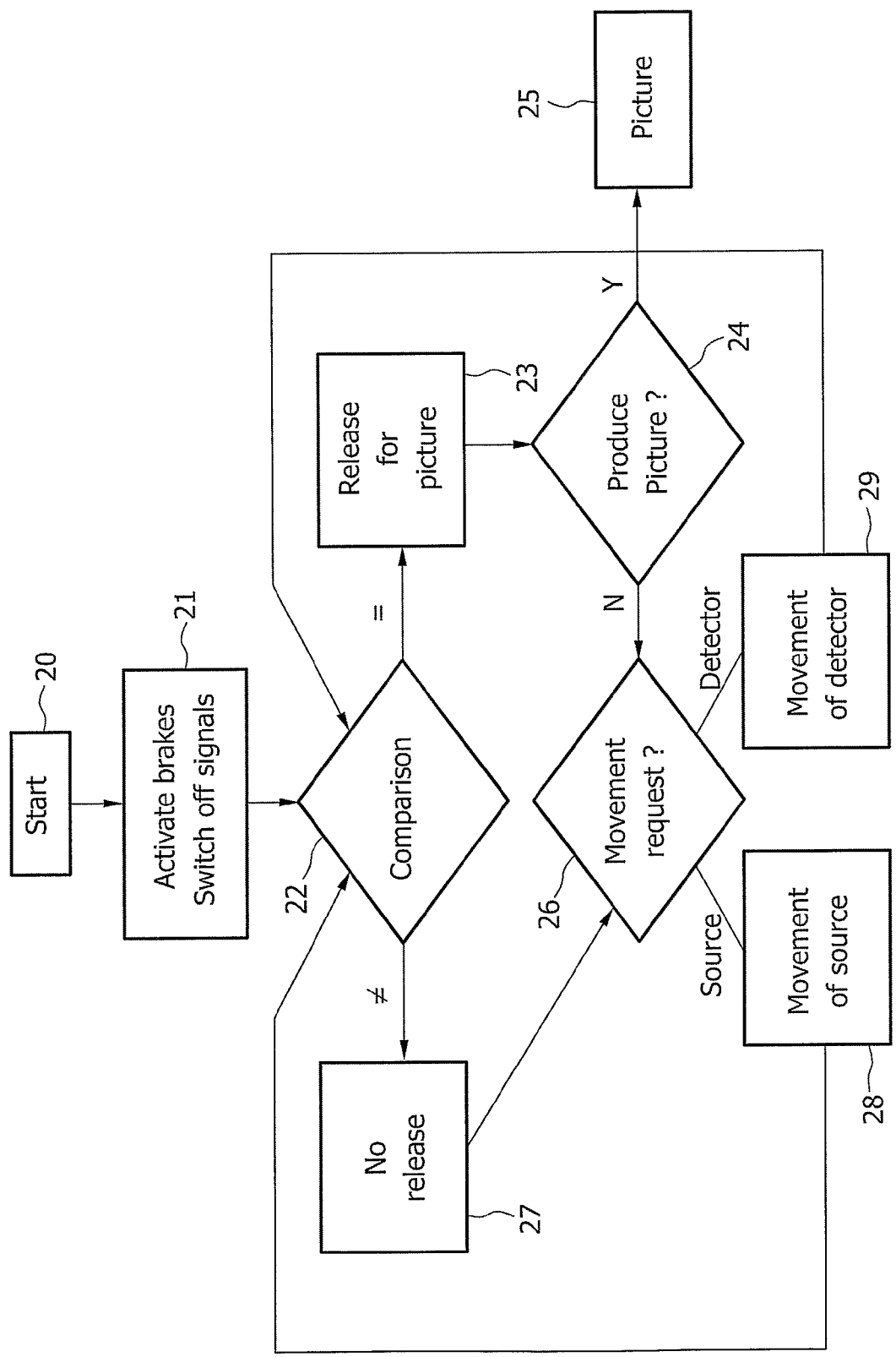
FIG. 2 shows a flow chart of a method according to the invention.

FIG. 2 shows a flow chart for a method according to the invention, for controlling the X-ray equipment 1. After the procedure is started in step 20, in a first step 21 the brakes are activated, and the signal device 9 is set so that no signals are output. Alternatively, a "ready" signal can be output. By means of a comparison 22, in the comparison device 8 the current setting of the X-ray equipment 1 is compared with a trigger setting. If they match, for example with a tolerance of 1% of the distance between the detector 4 and the source 2, or in the fact that in the case of movement that is possible only in discrete steps, the greatest possible approximation to a trigger setting is achieved, a release 23 of the X-ray equipment 1 is effected by means of the release device 14, and after a positive decision 24, in step 25 a picture is taken. In the standard IEC 60601-1-3 (X-ray directive), more detailed conditions for a trigger setting are laid down. If no picture is to be taken, an inquiry 26 takes place as to whether a setting alteration is to be made to the X-ray equipment. In the method according to the invention, this inquiry 26 is also reached where the comparison 22 yields non-equality, via an intermediate step 27 in which it is ascertained that there is no release for the X-ray equipment 1. Depending on whether, on the basis of this inquiry 26, a movement of the X-ray source 2 or of the X-ray detector 4 should take place, there follows a movement 28 of the X-ray source or a movement 29 of the X-ray detector, after which we then proceed once more to comparison 22, thus resulting in a loop.

In the case of the inquiry 26, as a further alternative it can be envisaged that the aperture arrangement 15 is altered, and corresponding further steps then result from that. It can also be envisaged that not all the setting possibilities are realized, in other words that for example only the position X1, Y1, Z1 and alignment Alfa1, Beta1 of the X-ray source 2 and the alignment Alfa2, Beta2 of the X-ray detector can be altered. The inquiry 26 can also take place such that no explicit inquiry takes place for example via a switching device, but that the detection devices 5a, 5b detect a desired movement by a change in the setting of the X-ray source or X-ray detector. Furthermore, there can be further differentiation, in that the individual setting possibilities along an x, y or z axis or around rotational axes are individually distinguished, and further separated movements are possible.

Figure 3:
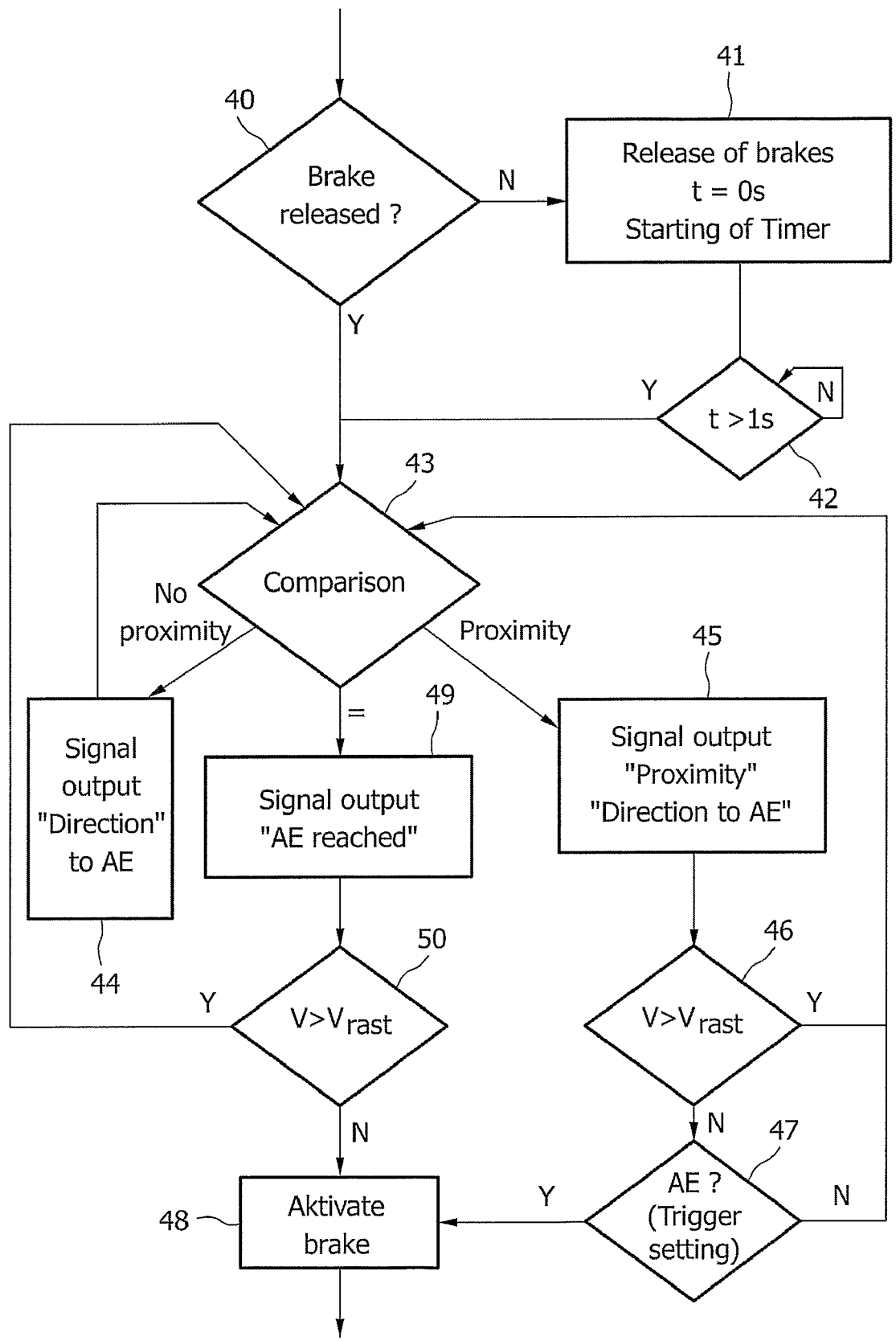
FIG. 3 shows a detailed flow chart of a part of the flow chart according to the invention as shown in FIG. 2.

FIG. 3 shows a flow chart of a part of the method according to the invention as shown in FIG. 2, in particular the steps 28 or 29. First of all a check is made to see whether the brake, for example a brake device 13a, 13b, is released. If not, in step 41 the brake is released, a timer is initialized, and this timer is started. In a delay loop 42, we wait for a predetermined period of time to expire, which in this case is given as 1 second. This delay loop 42 provides an opportunity to enable the alteration of the current setting if this would not otherwise be possible on account of the subsequent steps. Where the current setting already corresponds to a trigger setting, the brakes would—as illustrated below—automatically be activated and thus any alteration of the setting would be prevented.

The delay loop 42 is followed by step 43, as is also the case directly in the case of a released brake. In step 43, the current setting is compared to a trigger setting. In this comparison 43, it is checked whether the current setting corresponds to a trigger setting or is in proximity to it, and a method is established as to how a trigger setting can be reached.

By "proximity", we mean a range around the trigger setting in which it can be achieved with minimal alteration of the setting. For example, proximity can mean that the current position deviates by no more than 10% of the distance between the source 2 and detector 4 (film focus distance, FFD), and the current alignment deviates not more than 10° from a trigger setting.

If the comparison 43 does not yield any proximity to a trigger setting, then in step 44 a signal is output which indicates to the user how a trigger setting can be achieved. Subsequently, a new comparison 43 takes place, wherein the user can have changed the current setting in the meantime.

If the comparison 43 yields the result that the current setting does lie in proximity to a trigger setting, then in step 45 a corresponding signal is output that indicates this proximity. Just as in step 44, it is also indicated how a trigger position can be achieved. Next, the speed at which the respectively current setting may change is checked. If this speed V lies above a limit speed $V_{Rast}$, then a new comparison 43 takes place. The limit speed is that speed at which locking or fixing and stopping of the movement is still possible or desired. This speed results from the characteristics of the brake device 13a, 13b and of the X-ray equipment 1 in general. If the speed V now lies below or at the limit speed, then a comparison 47 takes place between the current setting and a trigger setting. If this comparison 47 does not yield equality in the sense of the invention, then step 43 follows once more. In the case of equality, in other words if a trigger setting has been reached, then the current setting is fixed by means of braking 48, and the procedure step for movement is concluded for the time being.

If the comparison 43 yields equality between the current setting and a trigger setting, then a corresponding signal is output (step 49). If, analogously to step 46, a check 50 yields the result that the speed is too high, then step 43 follows once more. If it is possible to fix the current setting, then this takes place in the following step 48.

It can furthermore be envisaged that in the close range around a trigger setting, the movement is not stopped, but slowly braked. With this, fixing of the current setting in the event of equality would not take place completely abruptly. It is also possible to do without the automatic braking or automatic fixing 48. The user would then have to effect fixing, or lifting of non-fixing, himself. The signals that are output can be of a lasting nature; in step 43 a respective lifting of these signals would then have to take place. The signals can also be so brief or short-lived that lifting is not necessary. It is also possible to envisage different limit speeds for the comparisons 46 and 50.

The X-ray equipment according to the invention has suitable sensors for all the settings that are relevant for X-ray equipment (position, angle, possibly aperture setting). Since the geometric relation between the X-ray source and X-ray detector is thus known, this information can be used to locate a trigger setting that enables an X-ray picture to be taken safely and effectively, to provide the user with instructions as to how he can achieve such a setting, and to control the X-ray equipment in such a way that only safe and effective X-ray pictures are taken. By avoiding elaborate setting devices for the position and alignment of the X-ray source and X-ray detector, both the X-ray equipment itself as well as its use are simplified and the safety is improved. Greater degrees of freedom are available to the user, he obtains better support from the system, and can thus improve the performance and the throughput rate of the system.

The invention claimed is:

1. X-ray equipment comprising:
    an X-ray source and an X-ray detector, at least one of which is configured for alteration as to its position and alignment;
    an aperture arrangement;
    a positioning device for positioning an examination object;
    a detection device for detecting position and alignment of one or more of said at least one of the X-ray source and the X-ray detector;
    an evaluation device for determining a suitable trigger setting for an X-ray picture, in which the X-ray source and the X-ray detector have positions (X1, Y1, Z1, X2, Y2, Z2) and alignments (Alfa1, Beta1, Alfa2, Beta2) appropriate for, through use of the X-ray equipment, taking an X-ray picture of the examination object;

a signal device for outputting signals that inform a user how, in terms of both position and alignment, said trigger setting is to be achieved; and a release device for releasing the X-ray equipment for an X-ray picture when the X-ray equipment has said trigger setting.

2. X-ray equipment as claimed in claim 1, wherein said aperture arrangement is adjustable, said X-ray equipment further comprising:

an aperture-arrangement-setting detection device for detecting a setting of said aperture arrangement, said evaluation device being designed for using the detected setting for determining said trigger setting.

3. X-ray equipment as claimed in claim 1, wherein said aperture arrangement is adjustable, said X-ray equipment further comprising:

an aperture determination device for determining a trigger aperture setting that, with the X-ray source and X-ray detector in said suitable trigger setting, is appropriate for, through use of the X-ray equipment, taking an X-ray picture of the examination object; and an aperture setting device for setting said aperture arrangement into the trigger aperture setting.

4. X-ray equipment as claimed in claim 1, comprising:

a comparison device for comparing a current position and alignment of at least one of the X-ray source and the X-ray detector with said trigger setting to be achieved, said signal device being configured for outputting signals that inform a user that the compared position and/or alignment lie in a predetermined range around said trigger setting to be achieved, and signals that inform the user that the compared position and/or alignment correspond to said trigger setting to be achieved.

5. X-ray equipment as claimed in claim 4, wherein among said signals that inform of said position and/or alignment lying in a predetermined range are signals that inform the user about how close a current X-ray equipment setting is to said trigger setting subject to comparison.

6. X-ray equipment as claimed in claim 1, comprising:

a brake device for at least one of fixing and releasing at least one of position and alignment of at least one of the X-ray source and the X-ray detector, and a control device for controlling the brake device.

7. X-ray equipment as claimed in claim 1, said suitable trigger setting being one of a pair of alternative trigger settings, said evaluation device being configured for determining said pair, one of the pair being based on keeping stationary a current position of said X-ray source, the other of the pair being based on keeping stationary said X-ray detector.

8. A method for controlling X-ray equipment comprising:

an X-ray source and an X-ray detector, at least one of which is configured for alteration as to its position and alignment;

an aperture arrangement; and a positioning device for positioning an examination object, said method comprising:

detecting position and alignment of one or more of said at least one of the X-ray source and the X-ray detector;

determining a suitable trigger setting for an X-ray picture, in which the X-ray source and the X-ray detector have positions (X1, Y1, Z1, X2, Y2, Z2) and alignments (Alfa1, Beta1, Alfa2, Beta2) appropriate for, through use of the X-ray equipment, taking an X-ray picture of the examination object;

outputting signals that inform a user how, in terms of both position and alignment, said trigger setting is to be achieved; and releasing the X-ray equipment for an X-ray picture when the X-ray equipment has said trigger setting.

9. The method as claimed in claim 8, wherein any current setting of said X-ray equipment is accommodated in that said outputting comprises outputting based on said current setting regardless of positions and alignments of said X-ray source and said X-ray detector that define said current setting.

10. The method as claimed in claim 8, said suitable trigger setting being one of a pair of alternative trigger settings, said determining comprising determining said pair, one of the pair being based on keeping stationary a current position of said X-ray source, the other of the pair being based on keeping stationary said X-ray detector.

11. An X-ray apparatus comprising:

an X-ray source configured for alteration in respect of its position and/or alignment;

an aperture arrangement;

a positioning device for positioning an examination object;

an X-ray detector configured for alteration in respect of its position and/or alignment;

a detection device for detecting the position and/or alignment of the X-ray source and/or of the X-ray detector;

an evaluation device for determining at least one suitable trigger setting for an X-ray picture, in which the X-ray source and the X-ray detector have positions (X1, Y1, Z1, X2, Y2, Z2) and alignments (Alfa1, Beta1, Alfa2, Beta2) appropriate for, through use of said X-ray apparatus, taking an X-ray picture of the examination object;

a signal device for outputting signals that inform a user how a trigger setting from among said at least one suitable trigger setting is to be achieved; and a release device for releasing said X-ray apparatus for an X-ray picture when said X-ray apparatus has a trigger setting from among said at least one suitable trigger setting, wherein said evaluation device is configured for determining a pair of alternative trigger settings, one of the pair being based on keeping stationary a current position of said X-ray source, the other of the pair being based on keeping stationary said X-ray detector.

12. The X-ray apparatus as claimed in claim 10, configured such that said trigger setting for which said user is informed on how it is to be achieved is determined, by said determining, before the informing of the user.

13. The X-ray apparatus as claimed in claim 11, further configured for outputting signals that inform said user of how each of said pair is achievable.

14. The X-ray apparatus as claimed in claim 13, further configured such that said signals that inform said user of how each of said pair is achievable inform said user by a separate notification device for each of said pair.

15. The X-ray apparatus as claimed in claim 11, configured for calculating what change to a current setting of the X-ray apparatus is necessary in order to achieve said trigger setting from among said at least one suitable trigger setting, said signal device being configured such that said outputting comprises informing said user of the calculated change.

16. The X-ray apparatus as claimed in claim 15, configured for said calculating with respect to both positions (X1, Y1, Z1, X2, Y2, Z2) and alignments (Alfa1, Beta1, Alfa2, Beta2).

17. The X-ray apparatus as claimed in claim 11, wherein said signal device is configured for outputting signals that inform a user how close a current setting of said X-ray apparatus is to a trigger setting from among said at least one suitable trigger setting.

18. The X-ray apparatus as claimed in claim 11, configured to accommodate any current setting of said X-ray apparatus in that said outputting comprises outputting based on said current setting regardless of positions and alignments of said X-ray source and said X-ray detector that define said current setting.

19. A computer software product for controlling X-ray equipment having an X-ray source configured for alteration as to its position and/or alignment, an aperture arrangement, a positioning device for positioning an examination object, and an X-ray detector configured for alteration as to its position and/or alignment, said computer software product comprising a computer readable medium embodying a computer program that includes instructions executable by a processor to perform a plurality of acts, said plurality comprising the acts of:

detecting the position and/or alignment of the X-ray source and/or of the X-ray detector;

determining at least one trigger setting that is suitable for an X-ray picture, in which the X-ray source and the X-ray detector have positions (X1, Y1, Z1, X2, Y2, Z2) and alignments (Alfa1, Beta1, Alfa2, Beta2) appropriate for, through use of the X-ray equipment, taking an X-ray picture of the examination object;

outputting signals that inform a user how a trigger setting from among said at least one trigger setting is to be achieved; and releasing the X-ray equipment for an X-ray picture when the X-ray equipment has a trigger setting from among said at least one trigger setting, wherein said determining comprises determining a pair of alternative trigger settings, one of the pair being based on keeping stationary a current position of said X-ray source, the other of the pair being based on keeping stationary said X-ray detector.

20. The computer software product as claimed in claim 19, wherein any current setting of said X-ray equipment is accommodated in that said outputting comprises outputting based on said current setting regardless of positions and alignments of said X-ray source and said X-ray detector that define said current setting.

* * * * *